United States Patent
Lambert et al.

(10) Patent No.: US 8,344,119 B2
(45) Date of Patent: Jan. 1, 2013

(54) **SYSTEM FOR THE PRODUCTION OF AROMATIC MOLECULES IN *STREPTOMYCES***

(75) Inventors: Fanny Lambert, Pegomas (FR); Joseph Zucca, Grasse (FR); Jean Mane, Grasse (FR)

(73) Assignee: V. Mane Fils, Bar sur Loup (FR)

(*) Notice: Subject to any disclaimer, the term of this patent is extended or adjusted under 35 U.S.C. 154(b) by 599 days.

(21) Appl. No.: 12/528,000

(22) PCT Filed: Feb. 20, 2008

(86) PCT No.: PCT/FR2008/050284
§ 371 (c)(1),
(2), (4) Date: Aug. 20, 2009

(87) PCT Pub. No.: WO2008/113936
PCT Pub. Date: Sep. 25, 2008

(65) Prior Publication Data
US 2010/0184172 A1    Jul. 22, 2010

(30) Foreign Application Priority Data
Feb. 21, 2007 (FR) ................................. 07 01229

(51) Int. Cl.
C07H 21/04 (2006.01)
C12N 1/21 (2006.01)
C12N 9/04 (2006.01)
C12P 7/24 (2006.01)
C12P 7/42 (2006.01)
C12P 7/22 (2006.01)

(52) U.S. Cl. .................... 536/23.2; 435/253.5; 435/147; 435/146; 435/156; 435/190

(58) Field of Classification Search ................ 536/23.2; 435/253.5, 147, 146, 156, 190
See application file for complete search history.

(56) References Cited

FOREIGN PATENT DOCUMENTS

| | | |
|---|---|---|
| EP | 0 885 968 A1 | 12/1998 |
| WO | WO 01/55342 A2 | 8/2001 |
| WO | WO 2007/099230 A2 | 9/2007 |
| WO | WO 2007/099231 A1 | 9/2007 |

OTHER PUBLICATIONS

French Search Report dated Aug. 23, 2007.
International Search Report dated Nov. 5, 2008.
Jacques A.E. Benen et al., "Molecular Cloning, Sequencing, and Heterologous Expression of the vaoA Gene from *Penicillium simplicissimum* CBS 170.90 Encoding Vanillyl-Alcohol Oxidase", The Journal of Biological Chemistry, Apr. 3, 1998, pp. 7865-7872, vol. 273, No. 14, The American Society of Biochemistry and Molecular Biology, Inc., XP-002410834.
Marco W. Fraaije et al., "Substrate specificity of flavin-dependent vanillyl-alchohol oxidase from *Penicillium simplicissimum*", Eur. J. Biochem., 1995, pp. 271-277, vol. 234, XP-000986081.

(Continued)

*Primary Examiner* — Rosanne Kosson
(74) *Attorney, Agent, or Firm* — Young & Thompson (57) ABSTRACT

A process for the production of natural ferulic acid, coniferyl alcohol and/or vanillin, includes the bio-conversion of eugenol by a bacteria belonging to the *Streptomyces* genes including at least one nucleotide sequence SEQ ID NO:1 or SEQ ID NO:8 or any nucleotide sequence having at least 70%, preferably 80% and very preferably 90%, identity with the sequence SEQ ID NO:1 or SEQ ID NO:8.

12 Claims, 3 Drawing Sheets

OTHER PUBLICATIONS

Jorg Overhage et al., "Harnessing eugenol as a substrate for production of aromatic compounds with recombinant strains of *Amycolatopsis* sp. HR167", Journal of Biotechnology, 2006, pp. 369-376, vol. 125, Elsevier B.V.

Jorg Overhage et al., "Highly Efficient Biotransformation of Eugenol to Ferulic Acid and Further Conversion to Vanillin in Recombinant Strains of *Escherichia coli*", Applied and Environmental Microbiology, Nov. 2003, pp. 6569-6576, vol. 69, No. 11, American Society for Microbiology, XP-002410833.

Rainer Plaggenborg et al., "Potential of *Rhodococcus* strains for biotechnological vanillin production from ferulic acid and eugenol", Applied Genetics and Molecular Biotechnology, 2006, pp. 745-755, vol. 72.

SYSTEM FOR THE PRODUCTION OF AROMATIC MOLECULES IN *STREPTOMYCES*

FIELD OF THE INVENTION

The present invention relates to the production of natural aromatic molecules. More particularly, the present invention relates to bioconversion in a bacterium of substrates, preferably eugenol, to phenol derivatives, in particular coniferyl alcohol and ferulic acid, said derivatives being usable for the production of natural vanillin used in food flavouring or perfumery (flavourings or fragrances).

BACKGROUND OF THE INVENTION

Vanillin (3-methoxy-4-hydroxybenzaldehyde) is the main component responsible for the olfactory and gustatory properties of the vanilla extract derived from *Vanillia planifolia* pods. It is one of the most used aromatic molecules in the industry. However, the production of natural vanillin from vanilla pods or vanilla extract only accounts for 20% of this market; its use is limited on the one hand because of the potential of available pods worldwide and on the other hand because of the widely fluctuating, high price of these pods (of the order of 30 £/kg to 450 £/kg i.e. a minimum of 1500 £/kg of natural vanillin potential).

Synthetic vanillin is therefore often used as an inexpensive substitute (approximately 15 £/kg) for natural vanillin for use in perfumery, cosmetics and in the food-processing industries. However, synthetic flavourings are less appreciated by consumers than natural flavourings.

It is for this reason that it is sought to obtain natural aromatic molecules, particularly vanillin, by biological processes, in particular bioconversion, which utilize microorganisms such as bacteria.

Within the meaning of the present invention, by bioconversion is meant the biological transformation of a substrate, preferably originating from a natural source, in order to obtain flavourings, fragrances or precursors of natural flavourings or fragrances.

Vanillin can be produced according to the following reaction diagram:

Several processes for producing natural molecules such as vanillin have already been described in the prior art.

In particular, the patent EP 0885968 describes a process for the production of vanillin in a bacterium belonging to the genus *Streptomyces*. This process comprises: a) the culture in a suitable medium of a bacterium belonging to the genus *Streptomyces* so as to form a fermentation broth, b) the addition of 5 to 40 gL-1 of ferulic acid to said broth in order to produce vanillin, and c) the extraction of the vanillin and guaiacol produced.

Another example described in the article by J. Overhage et al. discloses 1) the expression of the vanillyl-alcohol oxidase gene in *Escherichia coli* and 2) the expression of the genes calA (encoding coniferyl alcohol dehydrogenase) and calB (encoding coniferyl aldehyde dehydrogenase). This process would allow ferulic acid to be produced as the main product of the conversion of eugenol by the final recombinant strain *E. coli* XL1-Blue (pSKvaom-PcalAmcalB) (Highly efficient biotransformation of eugenol to ferulic acid and further conversion to vanillin in recombinant strains of *Escherichia coli*, 2003, Applied and Environmental Microbiology pp. 6569-6576). It is stated that the ferulic acid produced by this strain could act as a substrate for a second multi-recombinant *E. coli* strain (pSKechE/Hfcs) to produce natural vanillin (J. Overhage et al. Appl. Env. Microbiol. 65: 4837-4847, 1999).

A final example of the production of phenol derivatives from eugenol was described in the article "Harnessing eugenol as a substrate for production of aromatic compounds with recombinant strains of *Amycolatopsis* sp. HR167" (J Biotechnol. 2006 Sep. 18; 125(3):369-76. Epub 2006 May 4. Overhage J., Steinbuchel A., Priefert H.). This article discloses the expression of the vanillyl-alcohol oxidase gene in the *Amycolatopsis* sp. strain HR167, allowing the catalysis of the conversion of eugenol to coniferyl alcohol, coniferyl aldehyde, ferulic acid, guaiacol and vanillic acid.

These three examples of the production of natural vanillin precursors or natural vanillin itself have the drawback firstly of having a relatively high production cost due to the use of purified ferulic acid which is an expensive raw material, and secondly of being difficult to implement industrially due to 1) the use of non-food multi-recombinant strains and 2) the low yield of the bioconversions.

In order for a biological process using microorganisms to be profitable, it is preferable to use a widely available and very inexpensive substrate and a harmless and genetically stable microorganism. The inventors therefore sought to develop a process for the production of natural vanillin precursors or natural vanillin itself, which is simple to implement industrially, i.e. preferably comprising only one stage, and having a lower production cost than that of the prior art. The solution proposed by the invention is to use a low-cost and available natural substrate, which eugenol is, as well as a class 1 strain belonging to the genus *Streptomyces*, such as for example *Streptomyces griseus*.

SUMMARY OF THE INVENTION

Thus, an object of the present invention is a process for manufacturing vanillin or vanillin precursors, such as ferulic acid or coniferyl alcohol, or also a mixture comprising vanillin precursors and vanillin, by the bioconversion of eugenol, in a bacterium belonging to the genus *Streptomyces*. In a first embodiment, the process of the invention allows vanillin to be manufactured. In a second embodiment, the process of the invention allows ferulic acid to be manufactured. In a third embodiment, the process of the invention allows coniferyl alcohol to be manufactured. In a fourth embodiment, the process of the invention allows a mixture of coniferyl alcohol, ferulic acid and/or vanillin to be manufactured.

The process of the invention is implemented using a bacterium belonging to the genus *Streptomyces* comprising the sequence SEQ ID NO:1 or the sequence SEQ ID NO:8 or any nucleotide sequence having at least 70%, preferably 80%, very preferably 90%, identity with the sequence SEQ ID NO:1 or the sequence SEQ ID NO:8. The sequences SEQ ID NO:1 and SEQ ID NO:8 correspond to the vanillyl-alcohol oxidase gene present in the genome of the filamentous fungus *Penicillium simplicissimum*, said gene having been optimized to be read in a bacterium belonging to the genus *Streptomyces*.

The present invention therefore has the advantage of allowing the production in a single stage, via a biological catalyst, of natural vanillin, natural coniferyl alcohol and/or ferulic acid, essentially free of impurities and at a low cost.

Another object of the invention is a bacterium belonging to the genus *Streptomyces* comprising at least one nucleotide sequence SEQ ID NO:1 or SEQ ID NO:8 or any nucleotide sequence having at least 70%, preferably 80%, very preferably 90%, identity with the sequence SEQ ID NO:1 or SEQ ID NO:8. Preferably, the bacterium is *Streptomyces griseus*.

Another object of the invention is the nucleotide sequence SEQ ID NO:1 and the sequence SEQ ID NO:8. The original sequence of the vanillyl-alcohol oxidase is present in the genome of the filamentous fungus *Penicillium simplicissimum*. The codons present in the DNA of *Penicillium simplicissimum* cannot be used for transcription by a bacterium belonging to the genus *Streptomyces*. The inventors therefore replaced these codons with appropriate codons read by a bacterium belonging to the genus *Streptomyces*, so as to obtain an optimized nucleotide sequence (SEQ ID NO:1 and SEQ ID NO:8).

Another object of the invention is an expression vector comprising at least one nucleotide sequence SEQ ID NO:1 or at least one sequence SEQ ID NO:8.

By "vector" or "expression vector" is meant any DNA sequence into which fragments of foreign nucleic acid can be inserted, the vectors allowing foreign DNA to be introduced into a host cell. Some examples of vectors are plasmids, cosmids, yeast artificial chromosomes (YACs), bacterial artificial chromosomes (BACs) and P1-derived artificial chromosomes (PACs) or vectors derived from a virus.

In an embodiment of the invention, the expression vector comprising the nucleotide sequence SEQ ID NO:1 or the sequence SEQ ID NO:8 is a bifunctional vector which is specific to the bacteria belonging to the genus *Streptomyces*.

By bifunctional vector is meant any plasmid capable of replicating itself in two different host organisms because it has two different origins of replication and can therefore be used to transfer genes from one host to another. Within the meaning of the present invention, a specific bifunctional vector of the bacteria belonging to the genus *Streptomyces* is a vector comprising means allowing its expression in said bacteria. Preferably, the bifunctional vector comprises an oriT gene which allows intergeneric conjugation and in particular expression both in *E. coli* and in a bacterium belonging to the genus *Streptomyces*.

Very preferably, the expression vector used in the invention comprises: 1) sequences (either an integration gene or a replication gene) allowing the sequence SEQ ID NO:1 or the sequence SEQ ID NO:8 to be introduced into and maintained in the strain, 2) an antibiotic resistance gene, 3) sequences allowing the selection marker to be excised in the final industrial strain, 4) an origin of transfer (oriT) of the RP4 type allowing intergenic conjugation between *E. coli* and *Streptomyces*, 5) a strong promoter and 6) strong terminator for the expression of the sequence SEQ ID NO:1 or SEQ ID NO:8 and 7) an MCS sequence.

In an embodiment of the invention, the expression vector is chosen from an integrative vector or a highly replicative vector of the multicopy type. Preferably, the vector is chosen from the integrative vectors pFLA2 and pFLA3. These integrative vectors have the advantage of allowing simple or multiple integration of a gene of interest into the final strain. The excision of the selection marker allows the same vector to be re-used to transform the strain again and thus increase the number of copies of the gene of interest.

According to another preference, the highly replicative vector of the multicopy type is the vector pFLA4. This vector has the advantage of replicating itself several times in the host, thus ensuring a large number of copies of the gene of interest in the host.

DETAILED DESCRIPTION OF THE INVENTION

Another object of the invention is a process for the production of ferulic acid, coniferyl alcohol and/or vanillin, comprising the bioconversion of eugenol by a bacterium belonging to the genus *Streptomyces* comprising at least one nucleotide sequence SEQ ID NO:1 or SEQ ID NO:8 or any nucleotide sequence having at least 70%, preferably 80%, very preferably 90%, identity with the sequence SEQ ID NO:1 or SEQ ID NO:8.

Said bacterium is obtained by:
a) cloning of the nucleotide sequence SEQ ID NO:1 or SEQ ID NO:8 corresponding to the vanillyl-alcohol oxidase gene in an expression vector, preferably specific to the bacteria belonging to the genus *Streptomyces*,
b) transformation of the expression vector obtained in a) in a competent bacterium, preferably *E. coli* DH5α,
c) transfer of the expression vector comprising the sequence SEQ ID NO:1 or the sequence SEQ ID NO:8 (after reactivity tests on the enzyme produced) into *E. coli* ET12567 (pUZ8002)
d) transformation or conjugation of a bacterium belonging to the genus *Streptomyces* with the bacterium obtained in c).
e) selection of the best transformants obtained in d) in the presence of the eugenol substrate.

According to an embodiment of the invention, the sequence SEQ ID NO:1 or the sequence SEQ ID NO:8 is cloned in a expression vector, said vector preferably being a bifunctional vector specific to the bacteria belonging to the genus *Streptomyces*. In order to do this, the nucleotide sequence SEQ ID NO:1 or SEQ ID NO:8 included in a vector of the pUC57 type and said expression vector are first digested by one or more restriction enzymes. The sequence SEQ ID NO:1 or SEQ ID NO:8 is then inserted by simple ligation or any other means of insertion into the expression vector.

Bacteria of the *E. coli* DH5α type are transformed according to any known process with the ligation product (expression vector comprising the sequence SEQ ID NO:1 or SEQ ID NO:8). The bacteria containing the expression vector are then selected using the selection marker, preferably an antibiotic resistance gene, present on the expression vector. Advantageously, this selection marker is the thiostrepton-resistance gene.

Advantageously, the expression vector is then introduced, by transformation, into competent bacteria, preferably the *E. coli* ET12567 strain. The transformants are then selected according to the method described above.

Finally, the vanillyl-alcohol oxidase gene can be transferred into a bacterium belonging to the genus *Streptomyces* by conjugation or transformation. Said bacteria comprising the vanillyl-alcohol oxidase gene integrated or not integrated into their genome are selected according to the method described above.

The bacteria belonging to the genus *Streptomyces* and comprising the vanillyl-alcohol oxidase gene are then cultured under conditions allowing the expression of said gene and in the presence of eugenol.

Preferably, the bacteria are incubated in a medium the pH of which is less than 10, preferably comprised between 6 and 9.5, and preferably comprised between 7 and 9, and more preferably comprised between 7.5 and 8.5; and the temperature of which is comprised between 27 and 40° C., preferably between 27 and 39° C., more preferably between 29 and 37° C. and even more preferably between 36 and 37° C., or even equal to 37° C.

In a preferred embodiment, the process of the invention comprises:
1) the culture of a bacterium belonging to the genus *Streptomyces* comprising at least one nucleotide sequence SEQ ID NO:1 or SEQ ID NO:8 or any nucleotide sequence having at least 70%, preferably 80%, very preferably 90%, identity with the sequence SEQ ID NO:1 or SEQ ID NO:8,
2) the addition, in a single dose, of eugenol as a bioconversion substrate to the fermentation medium in a quantity comprised between 5 and 40 g/l, preferably 10 to 35 g/1,
3) the extraction of the coniferyl alcohol from the fermentation medium.

According to this process aimed at obtaining a majority level of conversion to coniferyl alcohol, the eugenol substrate is preferably added to the culture medium of said bacterium in a single dose and the quantity of eugenol introduced is comprised between 5 and 40 g/l, preferably from 10 to 25 g/l. Preferably, the eugenol solution added comprises a mixture of eugenol, glucose and oil or a mixture of eugenol, glycerol and oil.

Preferably, said bacteria are incubated in a medium the pH of which is comprised between 8 and 10, preferably between 7 and 9 and more preferably equal to 9. The aeration of the medium is preferably comprised between 0.1 and 1 L of air/min The medium is preferably stirred at less than 1000 rpm for 3 L of medium, and very preferably at 900 rpm for 3 L of medium. The temperature of the medium is preferably comprised between 27 and 40° C., preferably between 27 and 39° C., more preferably between 27 and 37° C. and very preferably is 37° C.

Under these conditions, the level of conversion of eugenol to coniferyl alcohol is generally comprised between approximately 50 and 95% for a quantity of introduced substrate varying from 10 to 25 g/l. The coniferyl alcohol is produced at a level of 10 to 25 g/l.

In a preferred embodiment, the process of the invention comprises:
1) the culture of a bacterium belonging to the genus *Streptomyces* comprising at least one nucleotide sequence SEQ ID NO:1 or SEQ ID NO:8 or any nucleotide sequence having at least 70%, preferably 80%, very preferably 90%, identity with the sequence SEQ ID NO:1 or SEQ ID NO:8,
2) the continuous addition of eugenol, as a bioconversion substrate, to the fermentation medium in a quantity comprised between 5 and 30 g/l, preferably 10 to 25 g/l,
3) the extraction of the ferulic acid from the fermentation medium.

According to this process aimed at obtaining a majority level of conversion to ferulic acid, the substrate is preferably added continuously to the culture medium of said bacterium and the final quantity of eugenol introduced is comprised between 5 and 30 g/l, preferably from 10 to 25 g/l. Preferably, the eugenol solution added comprises a mixture of eugenol, glucose and oil or a mixture of eugenol, glycerol and oil. Preferably, the eugenol solution is continuously added to the medium over 3 to 5 days at a flow rate comprised between 0.2 g/L/H and 0.12 g/L/H.

Preferably, said bacteria are incubated in a medium the pH of which is comprised between 8 and 10, preferably between 7 and 9 and more preferably between 7 and 8.5. The aeration of the medium is preferably comprised between 0.1 and 1 L of air/min The medium is preferably stirred at less than 1000 rpm for 3 L of medium, and very preferably at 900 rpm for 3 L of medium. The temperature of the medium is preferably comprised between 27 and 40° C., preferably between 27 and 39° C., more preferably between 27 and 37° C. and very preferably is 37° C. The flow rate of substrate into the 3 L fermenter is comprised between 0.05 g of eugenol/L/hour and 1 g of eugenol/L/hour. Preferably, the flow rate of eugenol is fixed between 0.15 and 0.7 g of eugenol/L/hour. Under these conditions, the level of conversion to ferulic acid is generally comprised between approximately 50 and 95% for a quantity of introduced substrate varying from 10 to 25 g/l. The ferulic acid is produced at a level of 10 to 25 g/l.

In a preferred embodiment, the process of the invention comprises:
1) the culture of a bacterium belonging to the genus *Streptomyces* comprising at least one nucleotide sequence SEQ ID NO:1 or SEQ ID NO:8 or any nucleotide sequence having at least 70%, preferably 80%, very preferably 90%, identity with the sequence SEQ ID NO:1 or SEQ ID NO:8,
2) the addition of eugenol, continuously or in a single dose, as a bioconversion substrate, to the fermentation medium in a quantity comprised between 5 and 50 g/l, preferably 10 to 35 g/l,
3) the extraction of the vanillin from the fermentation medium.

According to this process aimed at obtaining the highest possible level of conversion to natural vanillin, said bacteria are, preferably, incubated in a medium the pH of which is less than 10, preferably comprised between 7 and 9, and more preferably between 7.5 and 8.5. The aeration of the medium is preferably comprised between 0.1 and 1 L of air/min. The medium is preferably stirred at less than 1000 rpm for 3 L of medium, and very preferably at 900 rpm for 3 L of medium. The temperature of the medium is preferably comprised between 27 and 40° C., preferably between 27 and 39° C., more preferably between 27 and 37° C. and very preferably is 37° C.

Preferably, the quantity of eugenol added to the culture medium of said bacterium is comprised between 5 and 50 g/l, preferably from 10 to 35 g/l. The eugenol can be added continuously or in a single dose. Preferably, the eugenol solution added comprises a mixture of eugenol, glucose and oil or a mixture of eugenol, glycerol and oil. Preferably, when the eugenol solution is added continuously to the medium, the addition takes place over 3 to 5 days at a flow rate comprised between 0.2 g/L/H and 0.12 g/L/H.

The level of conversion to vanillin is comprised between 30 and 72% for a quantity of distributed eugenol varying from 10 to 35 g/l.

Another object of the invention is a process for the production of vanillin from ferulic acid by the same bacterium belonging to the genus *Streptomyces*. In fact, the strain naturally has the genetic and enzymatic make-up that allows it to carry out this reaction. Thus, whether or not it contains the sequence SEQ ID NO:1 or SEQ ID NO:8, it is capable of converting ferulic acid to vanillin It is in fact possible to verify that, under suitable conditions, the quantity of vanillin produced can be comprised between 10 and 25 g/l, preferably between 14 and 24 g/l when between 28 and 36 g/l of ferulic acid is administered to the strain.

According to another embodiment of the invention, the stage of conversion of the ferulic acid to vanillin is carried out by enzymatic or biochemical route, in particular using the processes described in the patents EP 0 606 441 and EP 0 804 606.

EXAMPLES

The present invention will be better understood with the aid of the following additional description which refers to examples of obtaining expression vectors comprising the sequence SEQ ID NO:1, bacteria belonging to the genus *Streptomyces* comprising these expression vectors and their use for the production, by bioconversion, of eugenol, ferulic acid and vanillin.

In the following examples, given by way of illustration, reference will be made to the attached figures, in which:

FIG. 1 corresponds to the expression vector pFLA2,
FIG. 2 corresponds to the expression vector pFLA3,
FIG. 3 corresponds to the expression vector pFLA4, 1—Obtaining the Sequence SEQ ID NO:1 Corresponding to the Vanillyl-Alcohol Oxidase which is Optimized for Transcription in Bacteria Belonging to the Genus *Streptomyces*.

Certain codons of the vanillyl-alcohol oxidase gene present in *Penicillium simplicissimum* are probably not read by the bacteria belonging to the genus *Streptomyces*. The codons considered as "probably not read" are those which have a frequency of use in the bacteria belonging to the genus *Streptomyces* of less than 10 per 1000. The frequency of use of the codons is given in the "codon usage database" (http://www.kasuka.or.jp/codon/). Based on the frequency of use of the codons in the bacteria belonging to the genus *Streptomyces*, the inventors created an optimum sequence SEQ ID NO:1 for the expression of the vanillyl-alcohol oxidase in these cells.

Restriction sites were introduced at the 5' and 3' ends to allow the cloning of the sequence in a vector. The added restriction sites are a function of the restriction sites present in the multiple cloning sites (MCSs) of the vectors.

Also introduced at the 3' end of the sequence are the STOP codons and the polyhistidine tail allowing a rapid purification of the enzyme produced on an Ni-NTA column.

The optimized sequence SEQ ID NO:1 is synthesized in the pUC57 plasmid by GenScript.

2—Construction of Four Expression Vectors Comprising the Sequence SEQ ID NO:1: pFLA2, pFLA3 and pFLA4.

Figure 1:
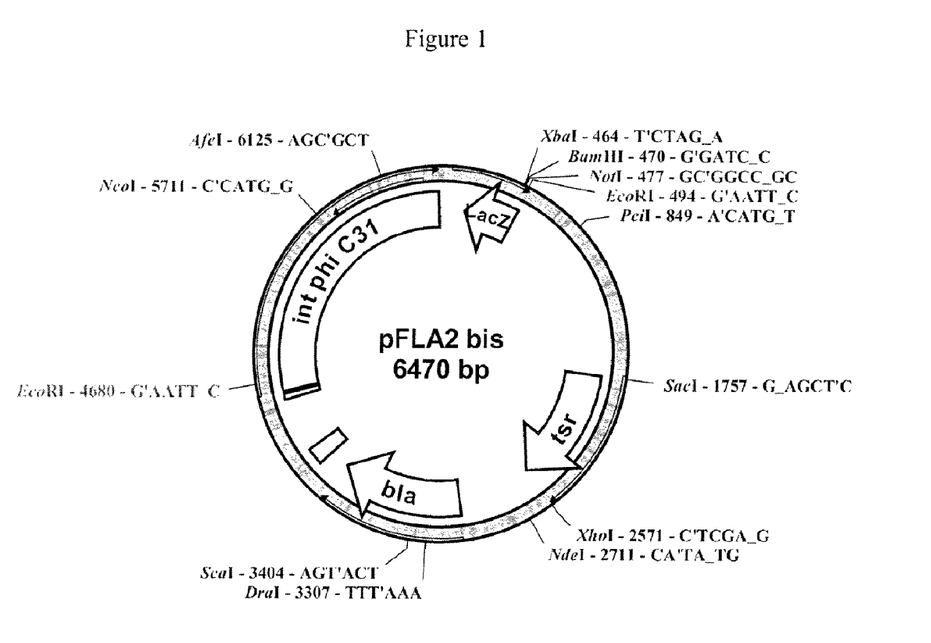

Construction of pFLA2 (FIG. 1):

The plasmid pRES19 was used as a source of the bla gene encoding beta-lactamase. The bla gene was amplified by PCR with the primers bla1F (5'CTCGAGAGACGAACTCCTTGAACC3', SEQ ID NO:2) and bla1R (5'GGCCTTACCAATGCTTAATCAG3', SEQ ID NO:3) in order to obtain a 1.4-kb fragment digested by the restriction enzymes XhoI and HaeIII. In the same way, the tsr gene of the plasmid pANT849 was amplified by the primers tsr1F (5'GAGCTCTGACTGAGTTGGACAC3', SEQ ID NO:4) and tsr1R (5'CTCGACTTATCGGTTGGCCG3', SEQ ID NO:5) and the fragment of 821 by obtained was digested by the enzymes SaI and XhoI. The 1.4-kb bla (at the XhoI/HaeIII ends) and 819-bp tsr (at the XhoI/NdeI ends) DNA fragments were cloned in the vector pSET152 digested by the restriction enzymes NaeI and Sad to form pFLA2b.

Figure 2:
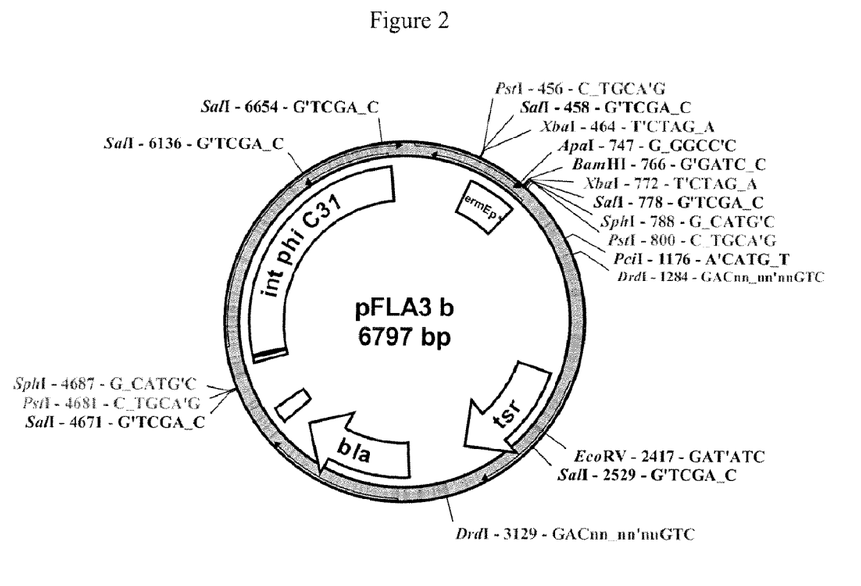

Construction of pFLA3 (FIG. 2):

In the expression vector pFLA3b, the LacZ gene of pFLA2b was replaced by a strong *Streptomyces* promoter: the promoter ermEp*. The ermEp* gene was synthesized in the pUC57 vector by GenScript Corporation and the insert was isolated by digesting the vector (pU57-ermEp) with the restriction enzymes XbaI and EcoRI.

The pFLA2b vector was also digested by the restriction enzymes XbaI and EcoRI in order to initiate the LacZ sequence and clone the ermEp* promoter by simple ligation between the two cleavage sites.

Figure 3:
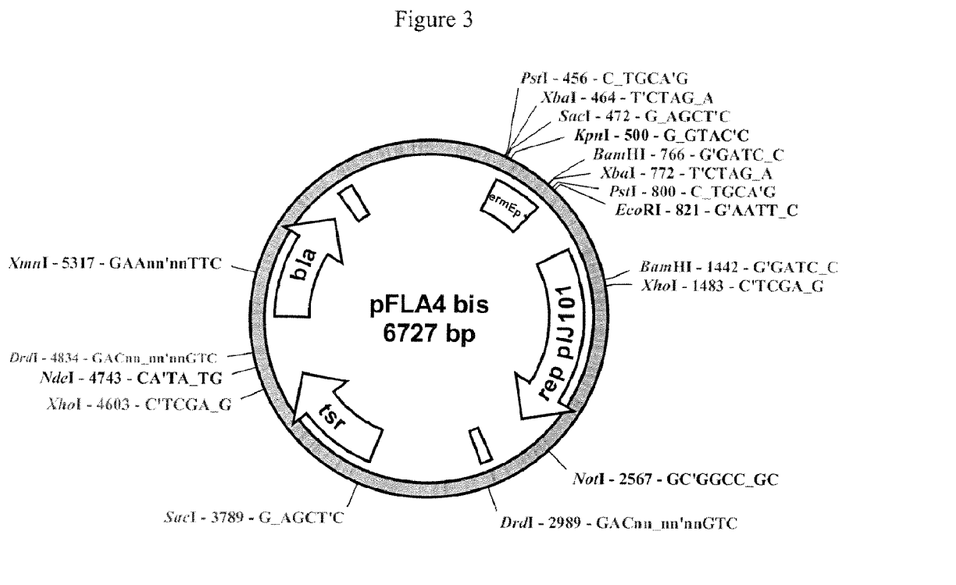

Construction of pFLA4 (FIG. 3):

The pFLA4b vector is constructed from the pFLA3b vector. The int phiC31 and attP genes are excised from the pFLA3 vector by an AfeI and SbfI endonuclease digestion. The cohesive end (3') generated by SbfI is released by the action of the S1 nuclease and the two ends are connected by simple ligation. 1771 by are thus eliminated from the pFLA3b vector in order to obtain the pFLA3-2b vector. A 1.8-kb nucleotide fragment comprising the rep gene, allowing autonomous replication of the vector in the host strain, is amplified by PCR on the pIJ101 vector isolated from *Streptomyces lividans* using the primers rep1F (5'ACATGTGTTAGTGCGAAGTGGGC3', SEQ ID NO:6) and resp1R (5'CTGCGAGTTCAG3', SEQ ID NO:7). The PCR products were digested by the endonucleases PciI and DrdI and the insert obtained in this way was cloned in the pFLA3-2b vector between the PciI and DrdI sites in order to obtain the pFLA4b vector of 6727 bp.

The sequence SEQ ID NO:1 comprises the BamHI (GGATCC) (5') and XbaI (3') ends, when the cloning is provided in the pFLA2 vector.

The sequence SEQ ID NO:1 comprises the ApaI (5') and BamHI (GGATCC) (3') ends, when the cloning is provided in the pFLA3 vector.

The sequence SEQ ID NO:1 comprises the KpnI (GGTACC) (5') and XbaI (TCT AGA) (3') ends, when the cloning is provided in the pFLA4 vector.

3—Transfer of the Sequence SEQ ID NO:1 into a Bacterium Belonging to the Genus *Streptomyces*

*E. coli* DH5α bacteria are transformed with one of the previously constructed vectors comprising the sequence SEQ ID NO: 1. These vectors are then introduced, in a second phase into the *E. coli* ET12567 (pUZ8002) strain rendered competent. This strain is deficient in methylation, which avoids the restrictions on the DNA when this is introduced into a bacterium belonging to the genus *Streptomyces*.

The transformants obtained are selected in the presence of the antibiotic

Apramycin: the resistant strains are those which comprise the sequence SEQ ID NO:1.

The sequence SEQ ID NO:1 is then transferred into *Streptomyces griseus* by conjugation. The exconjugants are again selected for their resistance to apramycin.

The strains *Streptomyces* 92873 and *Streptomyces* sp 92286 were transformed with one of the previously constructed vectors and two recombinant strains were selected.

These strains, comprising at least one copy of the sequence SEQ ID NO:1, are named *Streptomyces* sp 92873 and *Streptomyces* sp 92286 respectively.

The production level of vanillyl-alcohol oxidase was estimated by carrying out cultures of the transformed strain on a Strepto medium and an SDS-PAGE analysis of the total extracts of bacteria. The analysis confirms the presence of a protein with the expected size of 64 KDa. The quantity produced is estimated between 0.5 and 5 μg of VAO per ml of culture for a dry weight of 8 g/L of cells.

4—Enzymatic Activity of the Vanillyl-Alcohol Oxidase Expressed in the *E. coli* DH5α Strains Comprising the Sequence SEQ ID NO:1

The bacterial cells are cultured from a stock kept at −80° C. and the expression of the VAO is essential because of the strong promoters used in the cloning vectors. The cells are then sonicated and the total extract (T-fraction) centrifuged to eliminate the cellular debris and reveal the presence of VAO in the soluble fraction. The SDS-PAGE analysis shows that the VAO protein the expected theoretical size of which is approximately 64.7 kDa is indeed produced. The majority of it is soluble. As the cloned protein comprises a polyhistidine tail at its N-terminal end, it is purified on a nickel column and the level of expression is analysed by SDS-PAGE. The quantity of vanillyl-alcohol oxidase produced in *E. coli* varies from 2 to 5 μg per ml of culture for an OD of 2.3 at 600 nm.

The enzymatic activity of the vanillyl-alcohol oxidase is analysed by conversion of the vanillic alcohol and the eugenol with the purified protein on an Ni NTA column from 10 ml of culture of *E. Coli* bacteria comprising the sequence SEQ ID NO: 1. The aromatic products derived from these conversions are analysed by HPLC.

It was possible to determine that the enzyme produced was indeed vanillyl-alcohol oxidase. The level of transformation with the purified enzyme is comprised between 85 and 92%. 0.74 mM of vanillin formed from 0.8 mM of vanillic alcohol and 0.69 mM of coniferyl alcohol formed from 0.8 mM of eugenol are measured.

The vanillic alcohol is converted to vanillin whether the enzyme is purified or the reaction takes place on a broth of *E. coli* DH5α cells. The optimum pH for the conversion lies between 7 and 10 and under these conditions, the quantity of vanillin produced varies from 0.41 to 1 g/l starting from 0.5 to 1 g/l of distributed vanillic alcohol.

The vanillyl-alcohol oxidase also catalyses the conversion of the eugenol to coniferyl alcohol. The gene cloned in *E. coli* DH5α encoding the VAO transforms up to 10 g/l of eugenol to coniferyl alcohol with a yield of 90% in a medium with a pH of 10. The reaction is just as effective with the purified enzyme as with a broth of recombinant *E. coli* DH5α cells.

5—Selection of the Recombinant Strains Comprising the Sequence SEQ ID NO:1

The purification of the enzyme by Ni NTA column and the analysis on SDS PAGE gel show that the protein produced by the transformants of the *Streptomyces* strains sp 92873 or sp 92286 is indeed vanillyl-alcohol oxidase.

The bacteria transformed with the expression vector containing the vanillyl-alcohol oxidase, as described above, were selected for their ability to consume eugenol and convert it to vanillin, ferulic acid or coniferyl alcohol depending on the experimental conditions. The *Streptomyces* strains sp 92286 and sp 92873 were selected as being the best candidates. The tests in Erlenmeyer flasks with *Streptomyces* strains comprising the sequence SEQ ID NO:1 reveal eugenol consumption levels varying from 75 to 90% depending on the bioconversion conditions.

The bioconversion conditions in Erlenmeyer flasks are as follows:

The transformed bacteria are cultured on a complete agar medium (YPD) then subcultured in 100 ml of liquid Strepto medium until the end of the exponential growth phase under the following conditions: 35° C., 175 rpm. The substrate is then added to the medium after the cells are taken up in a 0.5M phosphate buffer, pH 8.5, at a level of 2.5 g/l of eugenol. The bioconversion conditions are as follows: 35° C., 175 rpm, 48H. Daily monitoring allows the bioconversion yields to be calculated. The analyses are carried out by HPLC. All the phenol derivatives are measured and quantified.

The quantity of vanillic acid or vanillin synthesized by the best candidate is of the order of 1 to 2 g/l starting from 2.5 g/l of eugenol provided at the start of bioconversion.

6—Conversion of Eugenol to Natural Vanillin by a *Streptomyces* Strain Comprising the Sequence SEQ ID NO:1

The bioconversion of eugenol is optimized in a 3-liter fermenter. The level of conversion over 4 days is comprised between 30 and 72% for a quantity of distributed substrate varying from 10 to 25 g/l. The optimum pH conditions during the conversion are as follows: the pH is regulated between 7 and 10 and preferably between 7 and 9.

The aeration is comprised between 0.1 and 0.8 volume of air/volume of medium/min Stirring is at 900 rpm for 3 L of medium and the temperature regulated at 37° C. during the culture and conversion phases.

The Following is an Example of Fermentation Conditions:

Day 1: The transformed strain 92873 comprising the sequence SEQ ID NO:1 is cultured in a Strepto medium (yeast extract: 0.8%, glucose 3.2%) with a pH of 7.5 for 48 hours in a 3 L fermenter, at 37° C. and 900 rpm, with an aeration of 0.3 vvm.

Day 3: When the level of oxygen dissolved in the culture medium has been stabilized at 100% for at least 4 hours and the measurement of the glucose level in the medium indicates that this is completely spent, between 0.04% and 0.08% $MgSO_4$ is added into the medium.

Adding the Substrate:

The eugenol is added continuously over 3 days (15 g/l of glucose+200 g of oil added for 15 g/l of eugenol) at a flow rate of 0.2 g/l/H or over 5 days (in which case, the flow rate is 0.12 g/l/H). The fermentation conditions are as follows: pH regulated between 7 and 9, aeration comprised between 0.2 and 1 L air/min.

Day 6 or 8: Stopping of the conversion when the chromatography results confirm the end of the biotransformation.

Daily monitoring allows the bioconversion yields to be calculated. The analyses are carried out by HPLC. All the vanillic derivatives are measured and quantified.

The Following is Another Example of Fermentation Conditions:

Day 1: The transformed strain 92873 comprising the sequence SEQ ID NO:1 is cultured in a Strepto medium (yeast extract: 0.8%, glucose 3.2%) with a pH of 7.5 for 48 hours in a 3 L fermenter, at 37° C. and 900 rpm, with an aeration of 0.3 vvm.

Day 3: When the level of oxygen dissolved in the culture medium has been stabilized at 100% for at least 4 hours and the measurement of the glucose level in the medium indicates that this is completely spent, between 0.04% and 0.08% $MgSO_4$ is added to the medium.

Addition of the Substrate:

The eugenol is added continuously over 5 days (10 g/l of glucose+85 g/l of oil added for 20 g/l of eugenol) at a flow rate of 0.17 g/l/H. The fermentation conditions are as follows: pH regulated between 7 and 9, aeration comprised between 0.2 and 1 L air/min.

Day 6 or 8: Stopping of the conversion when the chromatography results confirm the end of the biotransformation.

Daily monitoring allows the bioconversion yields to be calculated. The analyses are carried out by HPLC. All the vanillic derivatives are measured and quantified.

The Following is Another Example of Conversion:
Day 1: The transformed strain 92873 comprising the sequence SEQ ID NO:1 is cultured in a Strepto medium (yeast extract: 0.8%, glucose 3.2%, $MgSO_4$ between 0.04% and 0.08%) with a pH of 7.5 for 48 hours in a 3 L fermenter, at 37° C. and 900 rpm, with an aeration of 1 L air/min.
Day 3: When the level of oxygen dissolved in the culture medium has been stabilized at 100% for at least 4 hours and the measurement of the glucose level in the medium indicates that this is completely spent, between 0.04% and 0.08% $MgSO_4$ is added to the medium.
Addition of the Substrate:
The eugenol is added in 1 single dose (10 g/l of glucose added for 10 g/l of eugenol) with the following fermentation conditions: the pH is regulated between 7 and 9 with soda, the aeration is comprised between 0.1 and 0.33 vvm.
Day 5: Stopping of the conversion when the chromatography results confirm the end of the biotransformation.
Daily monitoring allows the bioconversion yields to be calculated. The analyses are carried out by HPLC. All the vanillic derivatives are measured and quantified.

7—Conversion of Eugenol to Natural Ferulic Acid by a *Streptomyces* Strain Comprising the Sequence SEQ ID NO:1

The bioconversion of eugenol to ferulic acid is optimized in a 3-liter fermenter.

The level of conversion over 5 days is comprised between 30 and 90% for a quantity of distributed substrate varying from 10 to 25 g/l. The optimum pH conditions during the conversion are as follows: the pH is regulated between 7 and 10 and preferably at 7.

The aeration is comprised between 0.1 and 0.8 volume of air/volume of medium/min Stirring is at 900 rpm for 3 L of medium and the temperature regulated at 37° C. during the culture and conversion phases.

The Following is an Example of Fermentation Conditions:
Day 1: The transformed strain 92873 comprising the sequence SEQ ID NO:1 is cultured in a Strepto medium (yeast extract: 0.8%, glucose 3.2%) with a pH of 7.5 for 48 hours in a 3 L fermenter, at 37° C. and 900 rpm, with an aeration of 0.3 vvm.
Day 3: When the level of oxygen dissolved in the culture medium has been stabilized at 100% for at least 4 hours and the measurement of the glucose level in the medium indicates that this is completely spent, between 0.04% and 0.08% $MgSO_4$ is added to the medium.
Addition of the Substrate:
The eugenol is added continuously over 4 days (15 g/l of glucose+200 g of oil added for 15 g/l of eugenol) at a flow rate of 0.15 g/l/H. The fermentation conditions are as follows: pH regulated at 7, aeration comprised between 0.2 and 1 L air/min.
Day 7: Stopping of the conversion when the chromatography results confirm the end of the biotransformation.
Daily monitoring allows the bioconversion yields to be calculated. The analyses are carried out by HPLC. All the vanillic derivatives are measured and quantified. It is possible to obtain a vanillin, coniferyl alcohol, ferulic acid mixture.

8—Conversion of Eugenol to Natural Coniferyl Alcohol by a *Streptomyces* Strain Comprising the Sequence SEQ ID NO:1

The bioconversion of eugenol is optimized in a 3-liter fermenter. The level of conversion over 2 days is comprised between 40 and 95% for a quantity of distributed substrate varying from 10 to 25 g/l. The optimum pH conditions during the conversion are as follows: the pH is regulated between 7 and 10 and preferably between 7 and 9.

The aeration is comprised between 0.1 and 0.8 volume of air/volume of medium/min Stirring is at 900 rpm for 3 L of medium and the temperature regulated at 37° C. during the culture and conversion phases.

The Following is an Example of Conversion:
Day 1: The transformed strain 92873 comprising the sequence SEQ ID NO:1 is cultured in a Strepto medium (yeast extract: 0.8%, glucose 3.2%, $MgSO_4$ between 0.04% and 0.08%) with a pH of 7.5 for 48 hours in a 3 L fermenter, at 37° C. and 900 rpm, with an aeration of 1 L air/min.
Day 3: When the level of oxygen dissolved in the culture medium has been stabilized at 100% for at least 4 hours and the measurement of the glucose level in the medium indicates that this is completely spent, between 0.04% and 0.08% $MgSO_4$ is added to the medium.
Addition of the Substrate:
The eugenol is added in 1 single dose (10 g/l of glucose added for 10 g/l of eugenol) with the following fermentation conditions: the pH is regulated between 8 and 9 with soda 5M, the aeration is comprised between 0.1 and 0.33 vvm.
Day 4 or 5: Stopping of the conversion when the chromatography results confirm the end of the biotransformation.
Daily monitoring allows the bioconversion yields to be calculated. The analyses are carried out by HPLC. All the vanillic derivatives are measured and quantified.

9—Example of Extraction of the Vanillin from the Bioconversion Broth.

At the end of the culture, the broth is concentrated under partial vacuum then extracted hot with methylcyclohexane. After concentration of the solvent, the vanillin crystallizes. It is washed with ethanol and recrystallized so as to obtain an HPLC purity greater than 99.5%.

The invention claimed is:

1. A method for producing natural ferulic acid, coniferyl alcohol, vanillin or mixtures thereof, comprising:
   a) culturing a bacterium belonging to the genus *Streptomyces* in a fermentation medium comprising eugenol, said bacterium comprising the nucleotide sequence of SEQ ID NO:1 or SEQ ID NO:8, or a nucleotide sequence having at least 90% sequence identity with the nucleotide sequence of SEQ ID NO:1 or SEQ ID NO:8, wherein the polypeptide encoded by the polynucleotide has vanillyl alcohol oxidase activity; and
   b) isolating the ferulic acid, coniferyl alcohol, vanillin or mixtures thereof produced in step (a).

2. The method according to claim 1, comprising:
   adding eugenol, continuously or in a single dose, as a bioconversion substrate to the fermentation medium in a quantity between 5 g/l and 50 g/l; and
   extracting vanillin from the fermentation medium.

3. The method according to claim 1, comprising:
   adding eugenol, in a single dose, as a bioconversion substrate to the fermentation medium in a quantity between 5 g/l and 40 g/l; and
   extracting coniferyl alcohol from the fermentation medium.

4. The method according to claim 1, comprising:
   adding eugenol, continuously, as a bioconversion substrate to the fermentation medium in a quantity between 5 g/l and 30 g/l; and
   extracting ferulic acid from the fermentation medium.

5. The method according to claim 1, wherein said bacterium is cultured in a fermentation medium having a pH less than 10.

6. The method according to claim 1, wherein said bacterium is cultured at a temperature between 27° C. and 40° C.

7. The method according to claim 1, wherein said bacterium is obtained by:
   a) cloning the nucleotide sequence of SEQ ID NO:1 or SEQ ID NO:8 into an expression vector;
   b) transforming the expression vector obtained in step (a) into a competent *E. coli* bacterium;
   c) conjugating a bacterium belonging to the genus *Streptomyces* with the *E. coli* bacterium obtained in step (b); and
   d) selecting *Streptomyces* cells comprising the vector of step (a) obtained in step (c) in the presence of eugenol.

8. The method according to claim 1, wherein the vanillin, ferulic acid and/or coniferyl alcohol is produced in the fermentation medium at a level of 10 to 25 g/l.

9. The method according to claim 1, wherein the ferulic acid is converted to vanillin in said bacterium belonging to genus *Streptomyces* by a biochemical or enzymatic route.

10. The method according to claim 1, wherein the bacterium comprises the nucleotide sequence of SEQ ID NO:1 or SEQ ID NO:8.

11. The method according to claim 7, wherein the expression vector is a bifunctional vector.

12. The method according to claim 1, wherein said bacterium is cultured at a temperature between 36° C. and 37° C.

* * * * *

SEQUENCE LISTING

```
<160> NUMBER OF SEQ ID NOS: 8

<210> SEQ ID NO 1
<211> LENGTH: 1680
<212> TYPE: DNA
<213> ORGANISM: Artificial Sequence
<220> FEATURE:
<223> OTHER INFORMATION: Synthetic Nucleotide

<400> SEQUENCE: 1
atgtcgaaga  cccaagagtt  ccggccgctg  accctgccgc  cgaagctgtc  gctgtcggac      60
ttcaacgagt  tcatccagga  catcatccgc  atcgtcggct  cggagaacgt  cgaggtcatc     120
```

```
tcgtcgaagg accagatcgt cgacggctgc tacatgaagc cgacccacac ccacgacccg    180
caccacgtca tggaccagga ctacttcctg gcctcggcca tcgtcgcccc gcgcaacgtc    240
gccgacgtgc agtcgatcgt gggcctcgcc aacaagttct cgttcccgct ctggccgatc    300
tcgatcggcc gcaactcggg ctacggcggc gccgccccgc gcgtctcggg ctcggtcgtc    360
ctggacatgg gcaagaacat gaaccgcgtc ctggaggtca acgtcgaggg cgcctactgc    420
gtcgtcgagc cgggcgtcac ctaccacgac ctgcacaact acctggaggc caacaacctg    480
cgcgacaagc tgtggctgga cgtcccggac ctgggcggcg gctcggtcct gggcaacgcc    540
gtcgagcgcg cgtcggcta cccccgtac ggcgaccact ggatgatgca ctcgggcatg    600
gaggtggtgc tggccaacgg cgagctgctg cgcaccggca tgggcgccct gccggacccc    660
aagcgccccg agaccatggg cctgaagcct gaggaccagc cgtggtcgaa gatcgcccac    720
ctgttcccgt acggcttcgg cccgtacatc gacggcctgt tctcgcagtc gaacatgggc    780
atcgtgacca agatcggcat ctggctgatg ccgaacccgg gcggctacca gtcgtacctg    840
atcaccctgc cgaaggacgg cgacctgaag caggccgtcg acatcatccg cccgctgcgc    900
ctgggcatgg ccctgcagaa cgtcccgacc atccgccaca tcctgctgga cgccgccgtc    960
ctgggcgaca agcgctcgta ctcgtcgaag accgagccgc tgtcggacga ggagctggac   1020
aagatcgcca agcagctgaa cctgggccgc tggaacttct acggcgccct gtacggcccg   1080
gagccgatcc gccgcgtgct gtgggagacc atcaaggacg ccttctcggc catcccgggc   1140
gtgaagttct acttcccgga ggacaccccg gagaactcgg tcctgcgcgt ccgcgacaag   1200
accatgcagg gcatcccgac ctacgacgag ctgagtgga tcgactggct gccgaatggc   1260
gcccacctgt tcttctcgcc gatcgccaag gtctcgggcg aggacgccat gatgcagtac   1320
gccgtcacca agaagcgctg ccaggaggcc ggcctggact tcatcggcac cttcaccgtg   1380
ggcatgcgcg agatgcacca catcgtctgc atcgtcttca acaagaagga cctgatccag   1440
aagcgcaagg tccagtggct gatgcgcacg ctgatcgaca ctgcgccgc caacggttgg   1500 ggcgagtacc gcacgcacct ggccttcatg gaccagatca tggagacgta caactggaac   1560
aactcgtcgt tcctgcgctt caacgaggtc ctgaagaacg ccgtcgaccc gaacggcatc   1620
atcgccccgg gcaagtcggg cgtctggccg tcgcagtact cgcacgtcac ctggaagctg   1680
```

```
<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

<400> SEQUENCE: 2
ctcgagagac gaactccttg aacc                                             24

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
ggccttacca atgcttaatc ag                                               22

<210> SEQ ID NO 4
<211> LENGTH: 22
<212> TYPE: DNA
```

-continued

<213> ORGANISM: Artificial Sequence
<220> FEATURE:
<223> OTHER INFORMATION: Synthetic Primer

<400> SEQUENCE: 4
gagctctgac tgagttggac ac                                          22

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ctcgacttat cggttggccg                                             20

<210> SEQ ID NO 6
<211> LENGTH: 23
<212> TYPE: DNA
<213> ORGANISM: Artificial Sequence
<220> FEATURE:
<223> OTHER INFORMATION: Synthetic Primer

<400> SEQUENCE: 6
acatgtgtta gtgcgaagtg ggc                                         23

<210> SEQ ID NO 7
<211> LENGTH: 12
<212> TYPE: DNA
<213> ORGANISM: Artificial Sequence
<220> FEATURE:
<223> OTHER INFORMATION: Synthetic Primer

<400> SEQUENCE: 7
ctgcgagttc ag                                                     12

<210> SEQ ID NO 8
<211> LENGTH: 1810
<212> TYPE: DNA
<213> ORGANISM: Artificial Sequence
<220> FEATURE:
<223> OTHER INFORMATION: Synthetic Nucleotide

<400> SEQUENCE: 8
gatctagaga tatcgagaag ggagcggaca tacatgtcga agacccaaga gttccggccg    60
ctgaccctgc cgccgaagct gtcgctgtcg gacttcaacg agttcatcca ggacatcatc   120
cgcatcgtcg gctcggagaa cgtcgaggtc atctcgtcga aggaccagat cgtcgacggc   180
tcgtacatga agccgaccca cacccacgac ccgcaccacg tcatggacca ggactacttc   240
ctggcctcgg ccatcgtcgc cccgcgcaac gtcgccgacg tgcagtcgat cgtgggcctc   300
gccaacaagt tctcgttccc gctctggccg atctcgatcg gccgcaactc gggctacggc   360
ggcgccgccc cgcgcgtctc gggctcggtc gtcctggaca tgggcaagaa catgaaccgc   420
gtcctggagg tcaacgtcga gggcgcctac tgcgtcgtcg agccgggcgt cacctaccac   480
gacctgcaca actacctgga ggccaacaac ctgcgcgaca agctgtggct ggacgtcccg   540
gacctgggcg gcggctcggt cctgggcaac gccgtcgagc gcggcgtcgg ctacaccccg   600
tacggcgacc actggatgat gcactcgggc atggaggtgg tgctggccaa cggcgagctg   660
ctgcgcaccg gcatgggcgc cctgccggac cccaagcgcc ccgagaccat gggcctgaag   720
cctgaggacc agccgtggtc gaagatcgcc cacctgttcc cgtacggctt cggcccgtac   780

```
atcgacggcc tgttctcgca gtcgaacatg ggcatcgtga ccaagatcgg catctggctg    840
atgccgaacc cgggcggcta ccagtcgtac ctgatcaccc tgccgaagga cggcgacctg    900
aagcaggccg tcgacatcat ccgcccgctg cgcctgggca tggccctgca gaacgtcccg    960
accatccgcc acatcctgct ggacgccgcc gtcctgggcg acaagcgctc gtactcgtcg   1020
aagaccgagc cgctgtcgga cgaggagctg gacaagatcg ccaagcagct gaacctgggc   1080
cgctggaact tctacggcgc cctgtacggc ccggagccga tccgccgcgt gctgtgggag   1140
accatcaagg acgccttctc ggccatcccg ggcgtgaagt tctacttccc ggaggacacc   1200
ccggagaact cggtcctgcg cgtccgcgac aagaccatgc agggcatccc gacctacgac   1260
gagctgaagt ggatcgactg gctgccgaat ggcgcccacc tgttcttctc gccgatcgcc   1320
aaggtctcgg gcgaggacgc catgatgcag tacgccgtca ccaagaagcg ctgccaggag   1380
gccggcctgg acttcatcgg caccttcacc gtgggcatgc gcgagatgca ccacatcgtc   1440
tgcatcgtct tcaacaagaa ggacctgatc cagaagcgca aggtccagtg gctgatgcgc   1500
acgctgatcg acgactgcgc cgccaacggt tggggcgagt accgcacgca cctggccttc   1560
atggaccaga tcatggagac gtacaactgg aacaactcgt cgttcctgcg cttcaacgag   1620
gtcctgaaga acgccgtcga cccgaacggc atcatcgccc cgggcaagtc gggcgtctgg   1680
ccgtcgcagt actcgcacgt cacctggaag ctgggatccc accaccacca ccaccacgga   1740
tcctaataat tactaattaa ttggggaccc tagaggtccc cttttttatt ttaaaagata   1800
tcaagcttgc                                                          1810
```